(12) United States Patent
Matsuda

(10) Patent No.: US 12,171,752 B2
(45) Date of Patent: Dec. 24, 2024

(54) METHODS OF TREATING POST-COVID CONDITION(S)

(71) Applicant: MediciNova, Inc., La Jolla, CA (US)

(72) Inventor: Kazuko Matsuda, La Jolla, CA (US)

(73) Assignee: MediciNova, Inc., La Jolla, CA (US)

( * ) Notice: Subject to any disclaimer, the term of this patent is extended or adjusted under 35 U.S.C. 154(b) by 0 days.

(21) Appl. No.: 18/103,983

(22) Filed: Jan. 31, 2023

(65) Prior Publication Data

US 2023/0285367 A1 Sep. 14, 2023

Related U.S. Application Data

(60) Provisional application No. 63/305,483, filed on Feb. 1, 2022.

(51) Int. Cl.
  *A61P 43/00* (2006.01)
  *A61K 31/437* (2006.01)
  *A61K 45/06* (2006.01)

(52) U.S. Cl.
  CPC ............ *A61K 31/437* (2013.01); *A61K 45/06* (2013.01); *A61P 43/00* (2018.01)

(58) Field of Classification Search
  CPC ....... A61K 31/437; A61K 45/06; A61P 43/00; A61P 25/28; A61P 31/14
  See application file for complete search history.

(56) References Cited

U.S. PATENT DOCUMENTS

| | | | |
|---|---|---|---|
| 6,395,747 B1 | 5/2002 | Sakoda et al. | |
| 8,138,201 B2 | 3/2012 | Kalafer et al. | |
| 9,314,452 B2 | 4/2016 | Kalafer et al. | |
| 2006/0160843 A1 | 7/2006 | Johnson et al. | |
| 2009/0197823 A1 | 8/2009 | Barlow et al. | |
| 2021/0308109 A1 | 10/2021 | Iwaki et al. | |

FOREIGN PATENT DOCUMENTS

| | | | | |
|---|---|---|---|---|
| WO | WO-2006063048 A2 * | 6/2006 | ........... A61K 31/437 |
| WO | WO-2007/142924 A1 | 12/2007 | |
| WO | WO-2021214475 A1 * | 10/2021 | ......... A61K 31/4418 |
| WO | WO-2022/181219 A1 | 9/2022 | |

OTHER PUBLICATIONS

Farnoosh et al. Are Iranian Sulfur Mustard Gas-Exposed Survivors More Vulnerable to SARS-CoV-2? Some Similarity in Their Pathogenesis. Disaster Medicine and Public Health Preparedness, 1-7. https://doi.org/10.1017/dmp.2020.156 (Year: 2020).*
NT Contributor. Administration of drugs 3: parenteral | Nursing Times. Nursing Times. https://www.nursingtimes.net/archive/administration-of-drugs-3-parenteral-10-09-2011/ (Year: 2011).*
Magdy, R., Eid, R. A., Fathy, W., Abdel-Aziz, M. M., Ibrahim, R. E., Yehia, A., Sheemy, M. S., & Hussein, M. Characteristics and Risk Factors of Persistent Neuropathic Pain in Recovered COVID-19 Patients. Pain Medicine. https://doi.org/10.1093/pm/pnab341 (Year: 2021).*
Moriarty et al. Cognitive Impairment in Patients with Chronic Neuropathic or Radicular Pain: An Interaction of Pain and Age. Frontiers in Behavioral Neuroscience, 11. https://doi.org/10.3389/fnbeh.2017.00100 (Year: 2017).*
Cho, et al., "Allosteric Inhibition of Macrophage Migration Inhibitory Factor Revealed by Ibudilast," PNAS, vol. 107, No. 25, pp. 11313-11318 (2010).
Gibson et al., "The Inhibitory Profile of Ibudilast Against the Human Phosphodiesterase Enzyme Family," European Journal of Pharmacology, vol. 538, pp. 39-42 (2006).
Sanftner et al., "Cross-species comparisons of the pharmacokinetics of ibudilast," Xenobiotica, vol. 39, No. 12, pp. 964-977 (Nov. 2009). [Abstract].
Obernolte, R., et al. (1993) "The cDNA of a human lymphocyte cyclic-AMP phosphodiesterase (PDE IV) reveals a multigene family" Gene 129: 239-247.
Rile et al., "Potentiation of Ibudilast Inhibition of Platelet Aggregation in the Presence of Endothelial Cells," Thrombosis Research, 102 239-246 (2001). [Abstract].
Souness et al., "Possible Role of Cyclic AMP Phosphodiesterases in the Actions of Ibudilast on Eosinophil Thromboxane Generation and Airways Smooth Muscle Tone," British Journal of Pharmacology, 111:1081-1088 (1994).
Suzumura et al., "Ibudilast suppresses TNF.alpha production by glial cells functioning mainly as type III phosphodiesterase inhibitor in NCS," Brain Research, 837:203-212 (1999).
Takuma et al., "Ibudilast attenuates actrocyte apoptsis via cyclic GMP signaling pathway in an in vitro reperfusion model," British Journal of Pharmacology, 133:841-848 (2001).
Jeffery et al., "The preparation and characterization of poly(lactide-co-glycolide) microparticles. II. The Entrapment of a Model Protein Using a (water-in-oil)-in-water Emulsion Solvent Evaporation Technique," Pharm. Research, vol. 10, pp. 362-368 (1993).
Yang, et al., "The Emerging Role of Toll-Like Receptor 4 in Myocardial Inflammation," Cell Death and Disease, vol. 7 e2234, 10 pages (2016).
McGee et a., "The Encapsulation of a Model Protein in Poly (D, L lactide-co-glycolide) Microparticles of Various Sizes: an Evaluation of Process Reproducibility," Journal of Microencapsulation, 14(2), pp. 197-210 (1997).
Schultheiß et al., "The IL-1b, IL-6, and TNF cytokine triad is associated with post-acute sequelae of COVID-19," Cell Rep. Med.,3(6):100663, 19 pages (Jun. 2022).
International Search Report and Written Opinion issued in International Patent Application No. PCT/US2023/011931, dated Apr. 21, 2023.
Nct05513560: "Canadian Adaptive Platform Trial for Long COVID (Reclaim)", ClinicalTrials.gov archive, Aug. 22, 2022 (Aug. 22, 2022), xP093038936, Retrieved from the Internet: URL: https: //clinicaltrials.gov/ct2/history /NCT05513560?V_1= View#StudyPageTop {retrieved on Apr. 13, 2023] the whole document.

* cited by examiner

*Primary Examiner* — Yih-Horng Shiao
*Assistant Examiner* — Hoi Yan Lee
(74) *Attorney, Agent, or Firm* — Foley & Lardner LLP

(57) ABSTRACT

Disclosed is a method of treating post-COVID condition(s) in a patient in need thereof, the method comprising administering to the patient a therapeutically effective amount of ibudilast, or a pharmaceutical salt thereof.

20 Claims, 8 Drawing Sheets

METHODS OF TREATING POST-COVID CONDITION(S)

CROSS-REFERENCE TO RELATED APPLICATIONS

This application claims the benefit of priority to U.S. Provisional Application No. 63/305,483, filed on Feb. 1, 2022, the contents of which are incorporated by reference herein in their entirety.

BACKGROUND

Ibudilast has been widely used in Japan for relieving symptoms associated with ischemic stroke or bronchial asthma. In recent clinical trials, its use in the treatment of multiple sclerosis (MS), an inflammatory disease of the central nervous system, has been explored (News.Medical.Net; Pharmaceutical News, 2 Aug. 2005). As disclosed in this publication, this clinical trial was expected to treat "relapsing-remitting MS," however, no mention is made of progressive multiple sclerosis. In U.S. Pat. No. 6,395,747, ibudilast is disclosed as a treatment for multiple sclerosis, which is generally understood to mean relapsing and remitting multiple sclerosis, not progressive multiple sclerosis. U.S. Patent Application Publication No. 20060160843 discloses ibudilast for the treatment of intermittent and short term pain, however, this is not pain related to a progressive neurodegenerative disease. However, U.S. Pat. No. 9,314,452 discloses ibudilast as a treatment for amyotrophic lateral sclerosis, a progressive neurodegenerative disease. Similarly, U.S. Pat. No. 8,138,201 discloses ibudilast as a treatment for primary progressive multiple sclerosis and/or secondary progressive multiple sclerosis.

While the use of ibudilast for a number of varying indications has been reported to date, to the best of the inventors' knowledge, its use in treating post-COVID condition(s) (also known as "long COVID," "post-COVID syndrome," and "post-acute sequelae of SARS-COV-2") in patients has heretofore remained largely unexplored.

SUMMARY

In one aspect, a method of treating post-COVID condition(s) in a patient in need thereof is provided, the method comprising, consisting essentially of, or consisting of administering to the patient a therapeutically effective amount of ibudilast, or a pharmaceutical salt thereof.

In some embodiments, the post-COVID condition(s) may include anxiety, general pain or discomfort, fatigue, insomnia, cognitive impairment, depression, shortness of breath, post-traumatic stress disorder, joint pain, muscle pain, chest pain or tightness, palpitations, smell or taste dysfunction, sleep difficulties, hair loss, or rash.

In some embodiments, the post-COVID condition(s) includes cognitive impairment and the cognitive impairment includes one or both of memory lapse and impaired concentration.

In some embodiments, ibudilast, or the pharmaceutically acceptable salt thereof, is administered orally. In some embodiments, ibudilast, or the pharmaceutically acceptable salt thereof, is administered intravenously. In some embodiments, ibudilast, or the pharmaceutically acceptable salt thereof, is administered by subcutaneous injection. In some embodiments, ibudilast, or the pharmaceutically acceptable salt thereof, is administered by intramuscular injection. In some embodiments, ibudilast, or the pharmaceutically acceptable salt thereof, is administered by inhalation.

In some embodiments, ibudilast, or the pharmaceutically acceptable salt thereof, is administered for 1, 2, 3, 4, 5, 6, 7, 8, 9, or 10 days, or more. In some embodiments, ibudilast, or the pharmaceutically acceptable salt thereof, is administered for at least 2 months.

In some embodiments, ibudilast, or the pharmaceutically acceptable salt thereof, is administered at least once daily. In some embodiments, ibudilast, or the pharmaceutically acceptable salt thereof, is administered twice daily.

In some embodiments, the therapeutically effective amount of ibudilast, or the pharmaceutically acceptable salt thereof, is from 0.1 mg to 720 mg per day. In some embodiments, the therapeutically effective amount of ibudilast, or the pharmaceutically acceptable salt thereof, is from 30 mg to 200 mg per day. In some embodiments, the therapeutically effective amount of ibudilast, or the pharmaceutically acceptable salt thereof, is 60 mg to 600 mg daily. In some embodiments, the therapeutically effective amount of ibudilast, or the pharmaceutically acceptable salt thereof, is 100 mg to 480 mg daily. In some embodiments, the therapeutically effective amount of ibudilast, or the pharmaceutically acceptable salt thereof, is selected from the group consisting of 30 mg/day, 40 mg/day, 50 mg/day, 60 mg/day, 90 mg/day, 100 mg/day, 110 mg/day, 120 mg/day, 150 mg/day, 180 mg/day, 190 mg/day, 200 mg/day, 210 mg/day, 240 mg/day, 270 mg/day, 300 mg/day, 360 mg/day, 400 mg/day, 440 mg/day, 480 mg/day, 520 mg/day, 580 mg/day, 600 mg/day, 620 mg/day, 640 mg/day, 680 mg/day, and 720 mg/day.

In some embodiments, the therapeutically effective amount may be administered as a single dose or is divided into two, three, or four doses. In some embodiments, ibudilast is administered continually.

In some embodiments, ibudilast, or the pharmaceutically acceptable salt thereof, is the only active agent administered to the patient. In some embodiments, ibudilast, or the pharmaceutically acceptable salt thereof, is administered to the patient with at least one other active agent. In some embodiments, the at least one other active agent comprises or consists of a corticosteroid, a COX-2 (cyclooxygenase-2) inhibitor, a NSAID (non-steroidal anti-inflammatory drug), a SSRI (selective serotonin reuptake inhibitor), a SNRI (serotonin and norepinephrine reuptake inhibitor), a tricyclic antidepressant, an antihistamine, a beta-blocker, cannabidiol, ATP (adenosine triphosphate), ifenprodil tartrate, neurotropin, gabapentin, pregabalin, mirtazapine, or a combination of two or more thereof.

spike protein with LPS and vehicle, or "Omicron" spike protein with LPS and ibudilast using cells from donor 2.

Figure 1:
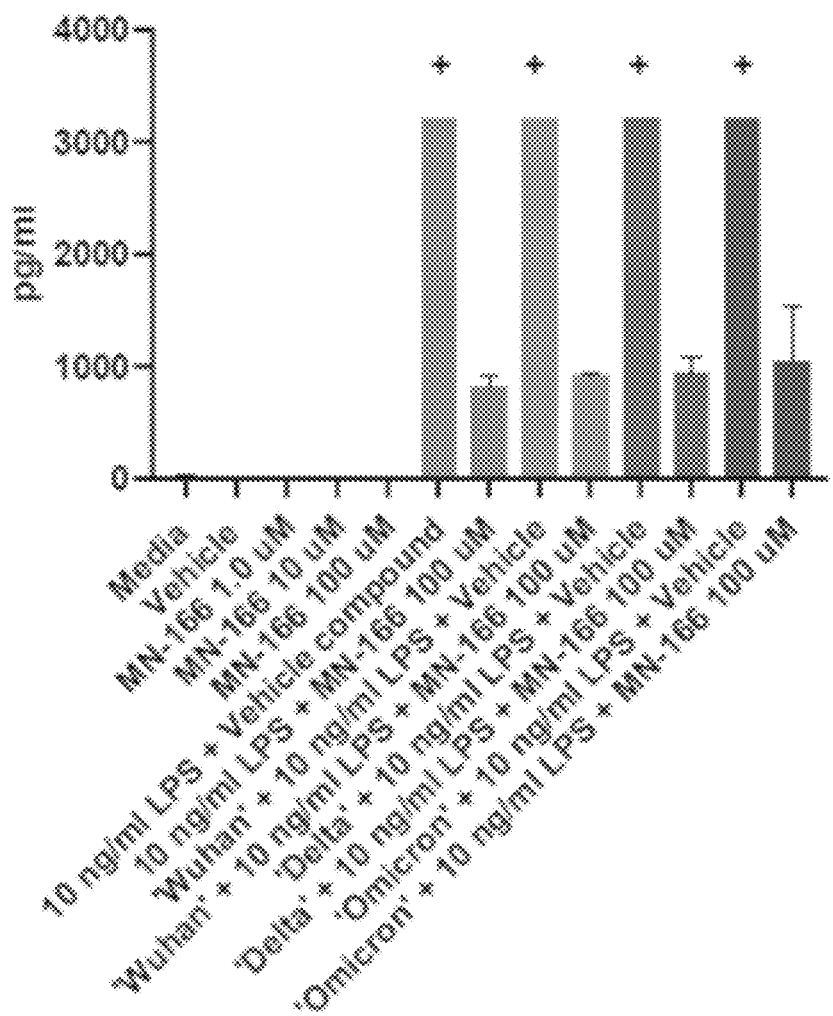
FIG. 1 depicts concentration of TNFα in the presence of media, vehicle, ibudilast alone (at 1, 10, or 100 µM), LPS with vehicle, LPS with ibudilast, "Wuhan" spike protein with LPS and vehicle, "Wuhan" spike protein with LPS and ibudilast, "Delta" spike protein with LPS and vehicle, "Delta" spike protein with LPS and ibudilast, "Omicron" spike protein with LPS and vehicle, or "Omicron" spike protein with LPS and ibudilast using cells from donor 1.
Figure 2:
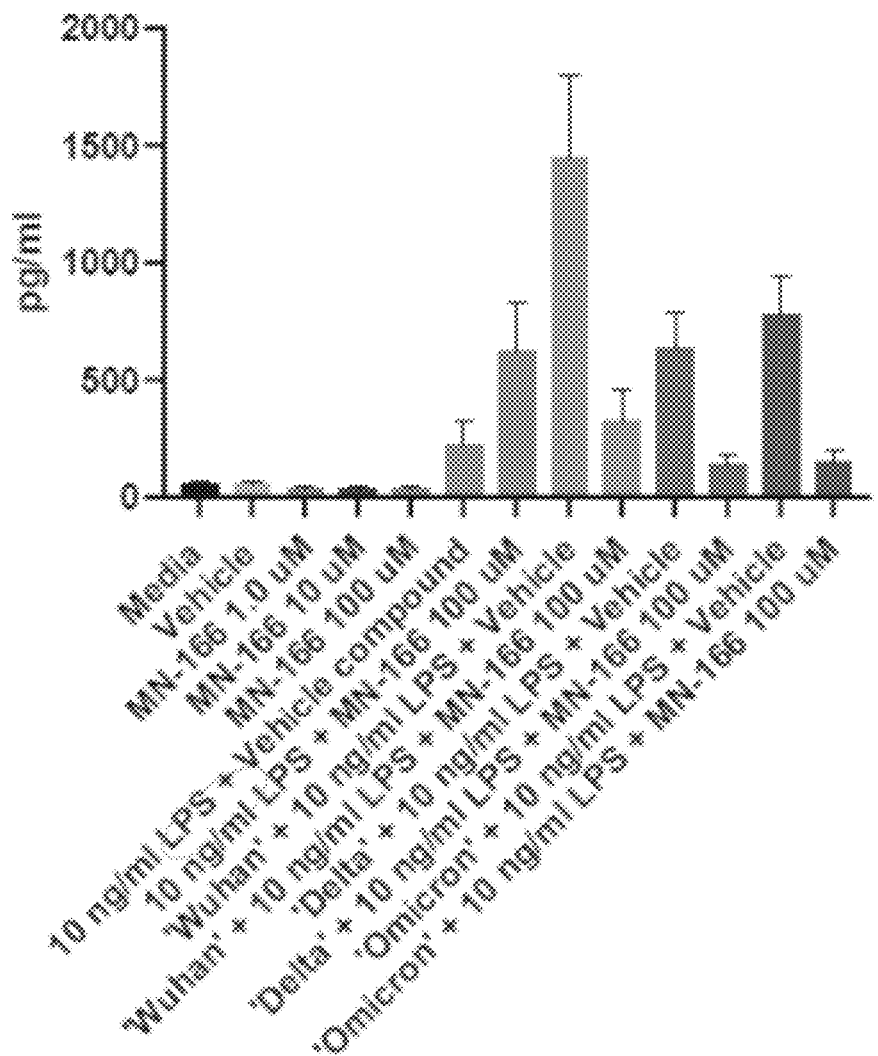
FIG. 2 depicts concentration of TNFα in the presence of media, vehicle, ibudilast alone (at 1, 10, or 100 µM), LPS with vehicle, LPS with ibudilast, "Wuhan" spike protein with LPS and vehicle, "Wuhan" spike protein with LPS and ibudilast, "Delta" spike protein with LPS and vehicle, "Delta" spike protein with LPS and ibudilast, "Omicron"
Figure 3:
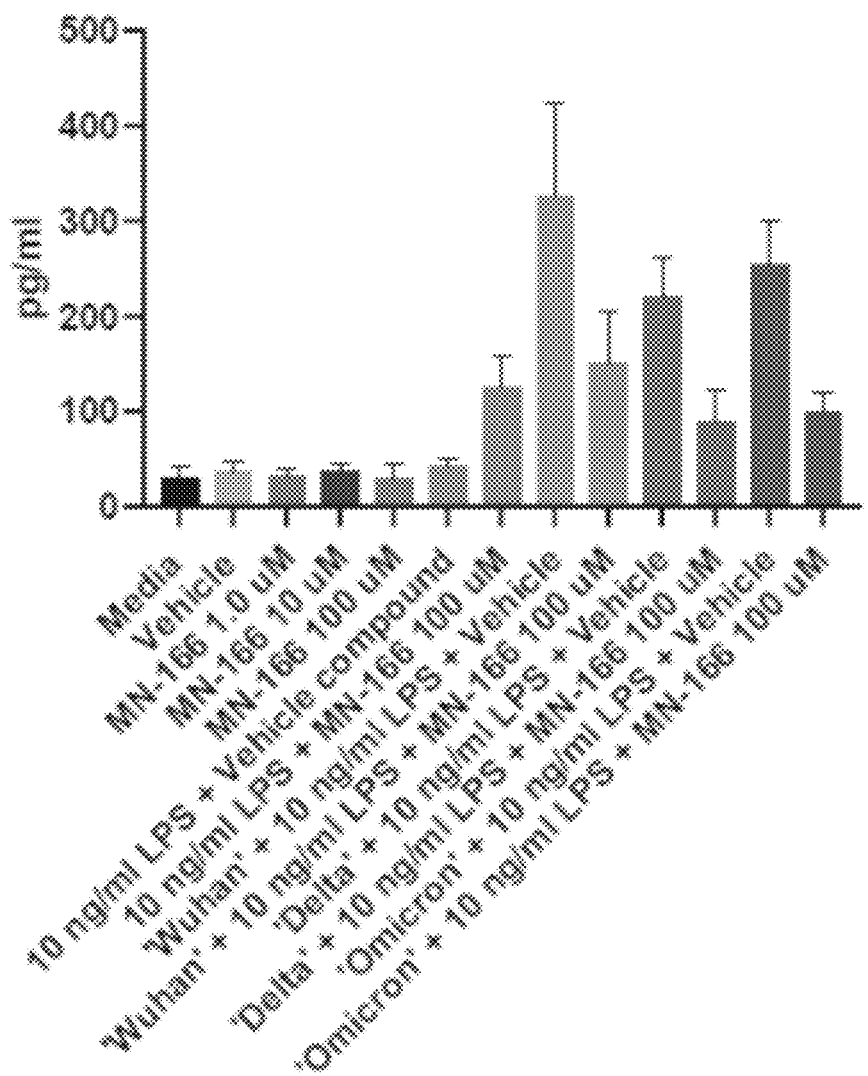

FIG. 3 depicts concentration of TNFα in the presence of media, vehicle, ibudilast alone (at 1, 10, or 100 µM), LPS with vehicle, LPS with ibudilast, "Wuhan" spike protein with LPS and vehicle, "Wuhan" spike protein with LPS and ibudilast, "Delta" spike protein with LPS and vehicle, "Delta" spike protein with LPS and ibudilast, "Omicron" spike protein with LPS and vehicle, or "Omicron" spike protein with LPS and ibudilast using cells from donor 3.

Figure 4:
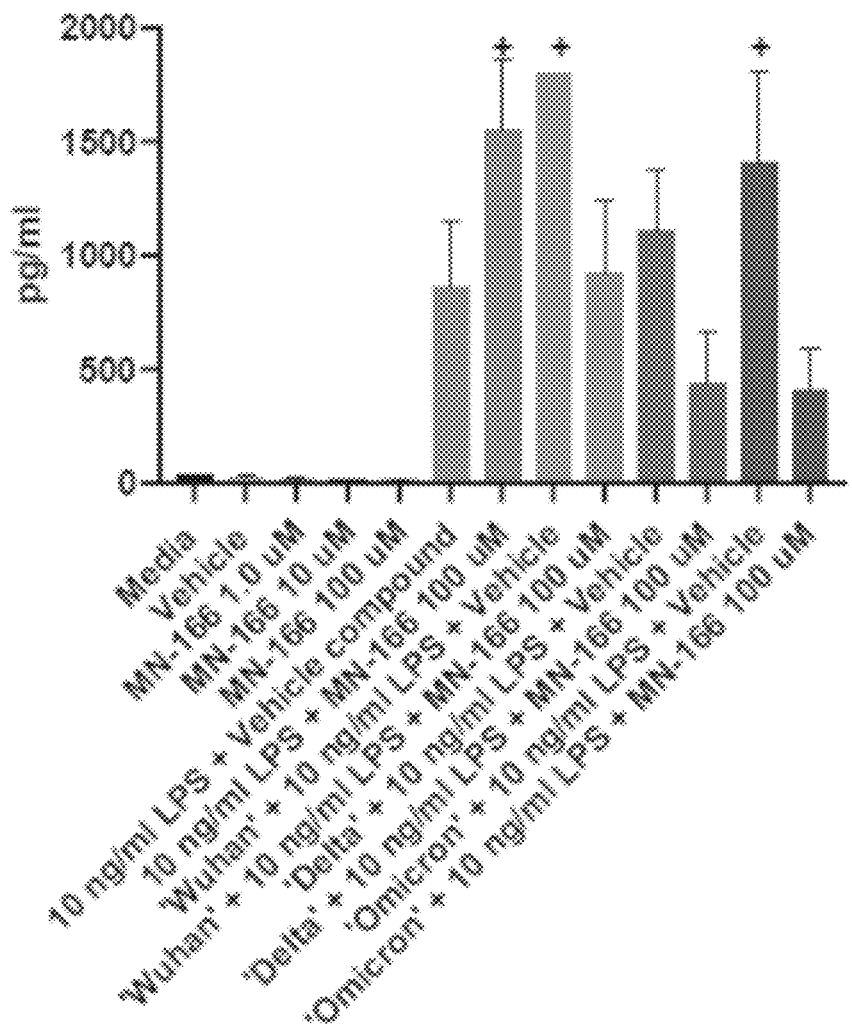

FIG. 4 depicts concentration of IL-6 in the presence of media, vehicle, ibudilast alone (at 1, 10, or 100 µM), LPS with vehicle, LPS with ibudilast, "Wuhan" spike protein with LPS and vehicle, "Wuhan" spike protein with LPS and ibudilast, "Delta" spike protein with LPS and vehicle, "Delta" spike protein with LPS and ibudilast, "Omicron" spike protein with LPS and vehicle, or "Omicron" spike protein with LPS and ibudilast using cells from donor 2.

Figure 5:
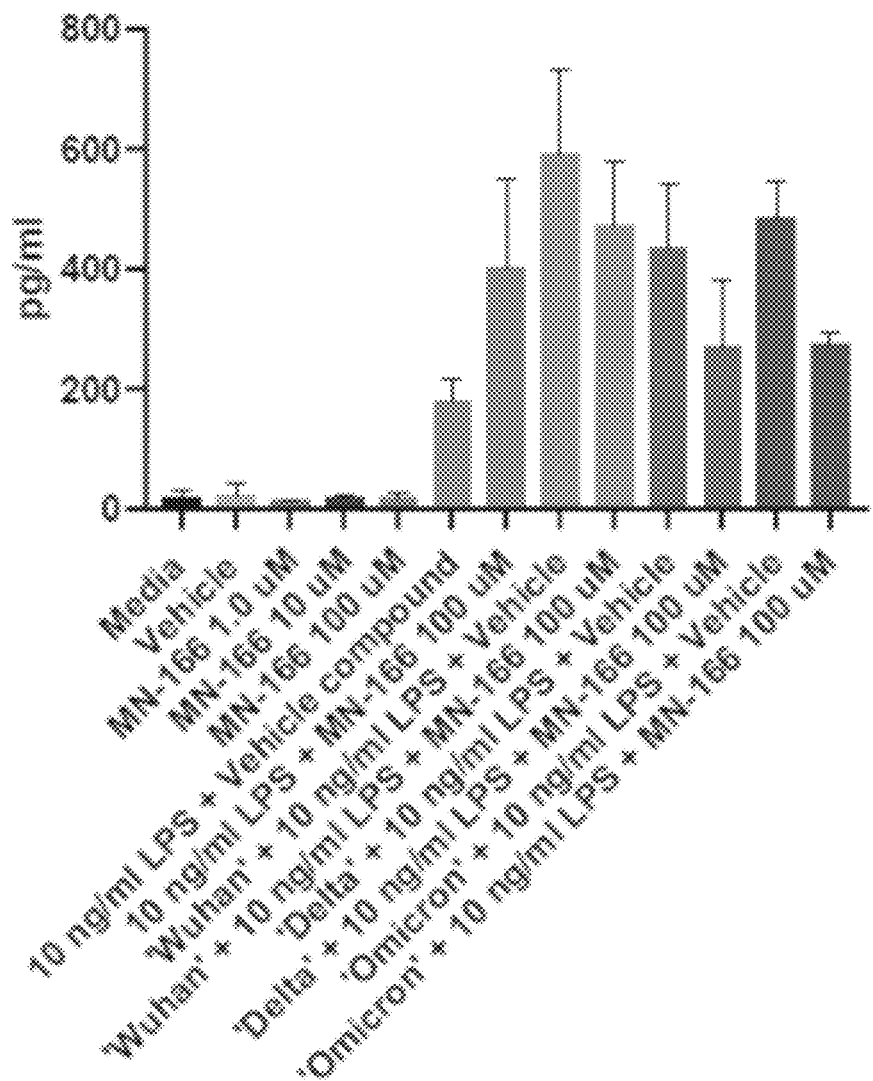

FIG. 5 depicts concentration of IL-6 in the presence of media, vehicle, ibudilast alone (at 1, 10, or 100 µM), LPS with vehicle, LPS with ibudilast, "Wuhan" spike protein with LPS and vehicle, "Wuhan" spike protein with LPS and ibudilast, "Delta" spike protein with LPS and vehicle, "Delta" spike protein with LPS and ibudilast, "Omicron" spike protein with LPS and vehicle, or "Omicron" spike protein with LPS and ibudilast using cells from donor 3.

Figure 6:
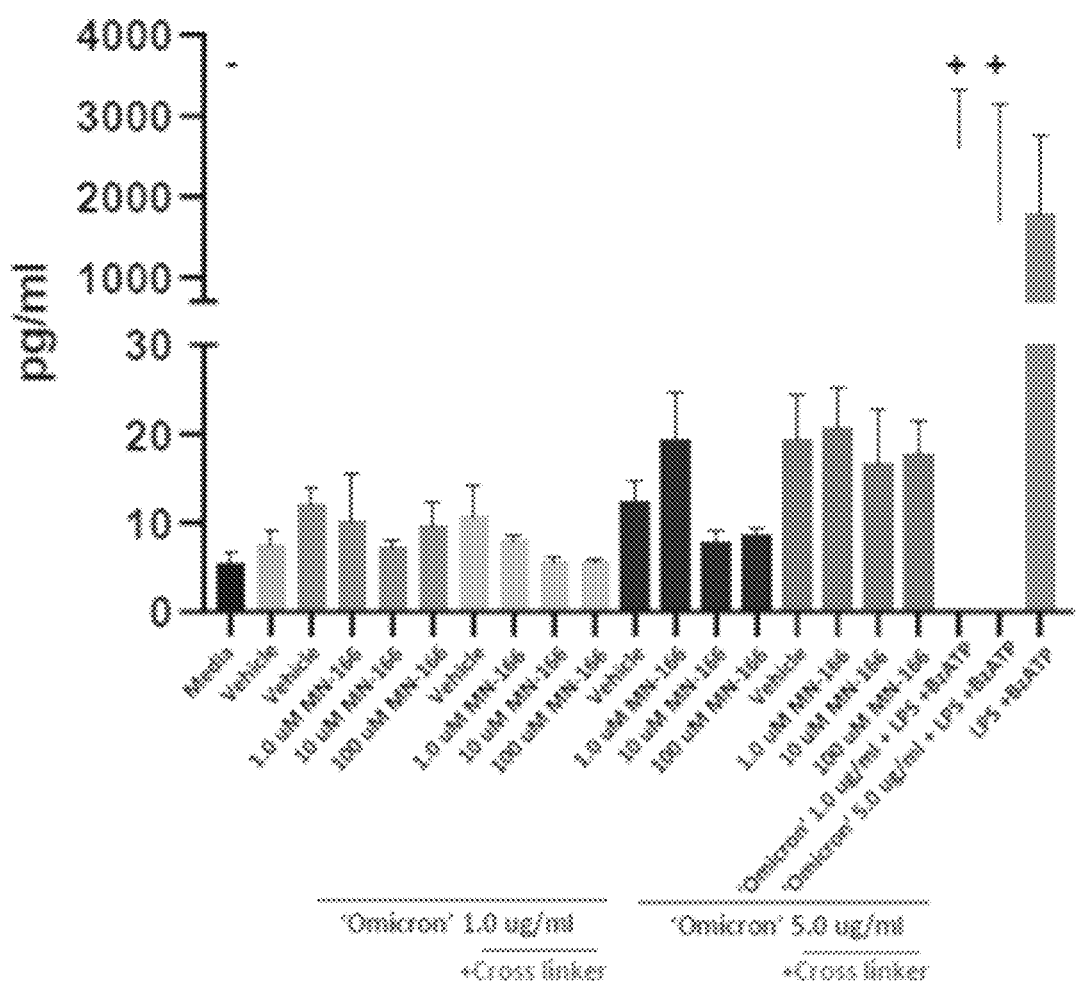

FIG. 6 depicts concentration of TNFα in the presence of media, vehicle, "Omicron" spike protein with vehicle, "Omicron" spike protein (1.0 µg/ml) with ibudilast (at 1, 10, or 100 µM), "Omicron" spike protein (1.0 µg/ml) with cross-linker and ibudilast (at 1, 10, or 100 µM), "Omicron" spike protein (5.0 µg/ml) with ibudilast (at 1, 10, or 100 µM), "Omicron" spike protein (5.0 µg/ml) with cross-linker and ibudilast (at 1, 10, or 100 µM), "Omicron" spike protein (1.0 µg/ml) with LPS and BzATP, "Omicron" spike protein (5.0 µg/ml) with LPS and BzATP, and LPS and BzATP using cells from donor 1.

Figure 7:
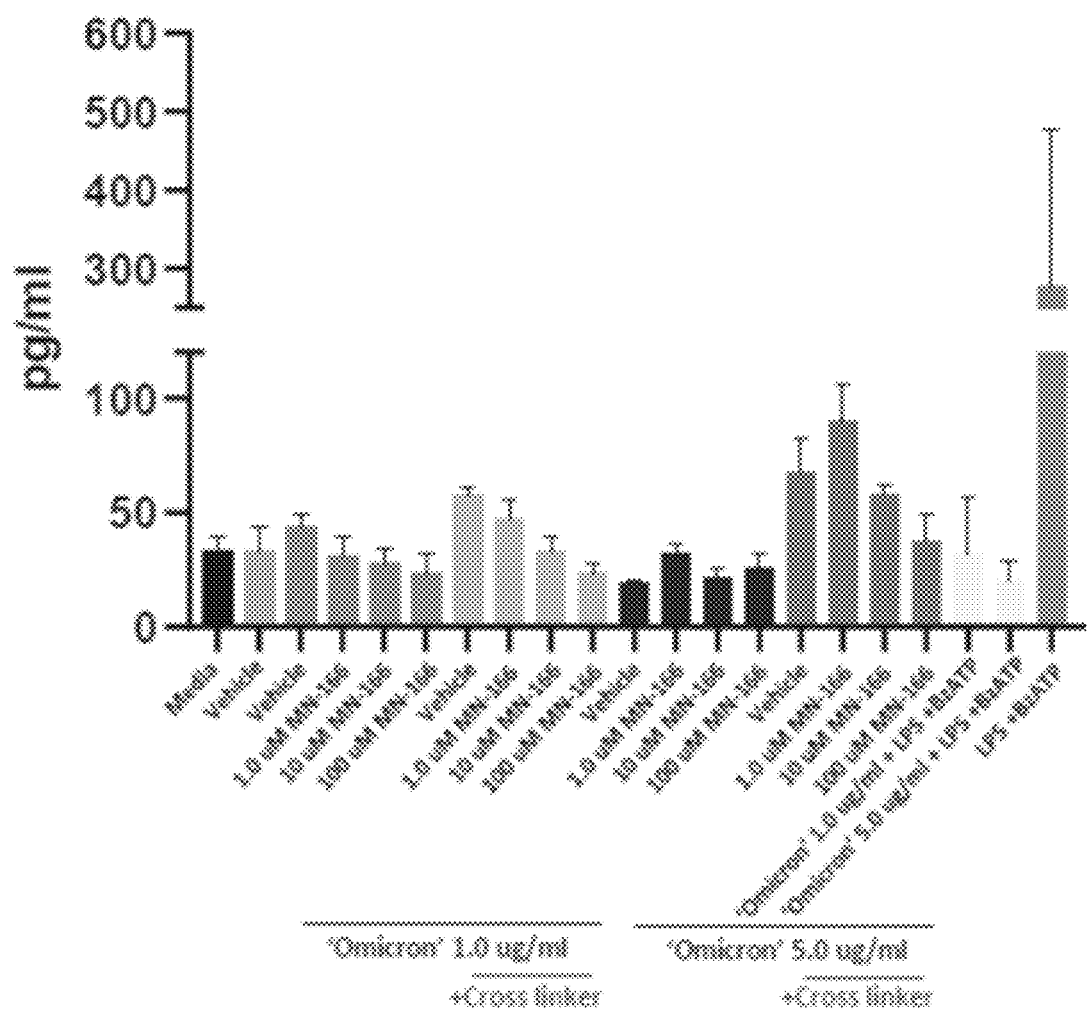

FIG. 7 depicts concentration of TNFα in the presence of media, vehicle, "Omicron" spike protein with vehicle, "Omicron" spike protein (1.0 µg/ml) with ibudilast (at 1, 10, or 100 µM), "Omicron" spike protein (1.0 µg/ml) with cross-linker and ibudilast (at 1, 10, or 100 µM), "Omicron" spike protein (5.0 µg/ml) with ibudilast (at 1, 10, or 100 µM), "Omicron" spike protein (5.0 µg/ml) with cross-linker and ibudilast (at 1, 10, or 100 µM), "Omicron" spike protein (1.0 µg/ml) with LPS and BzATP, "Omicron" spike protein (5.0 µg/ml) with LPS and BzATP, and LPS and BzATP using cells from donor 2.

Figure 8:
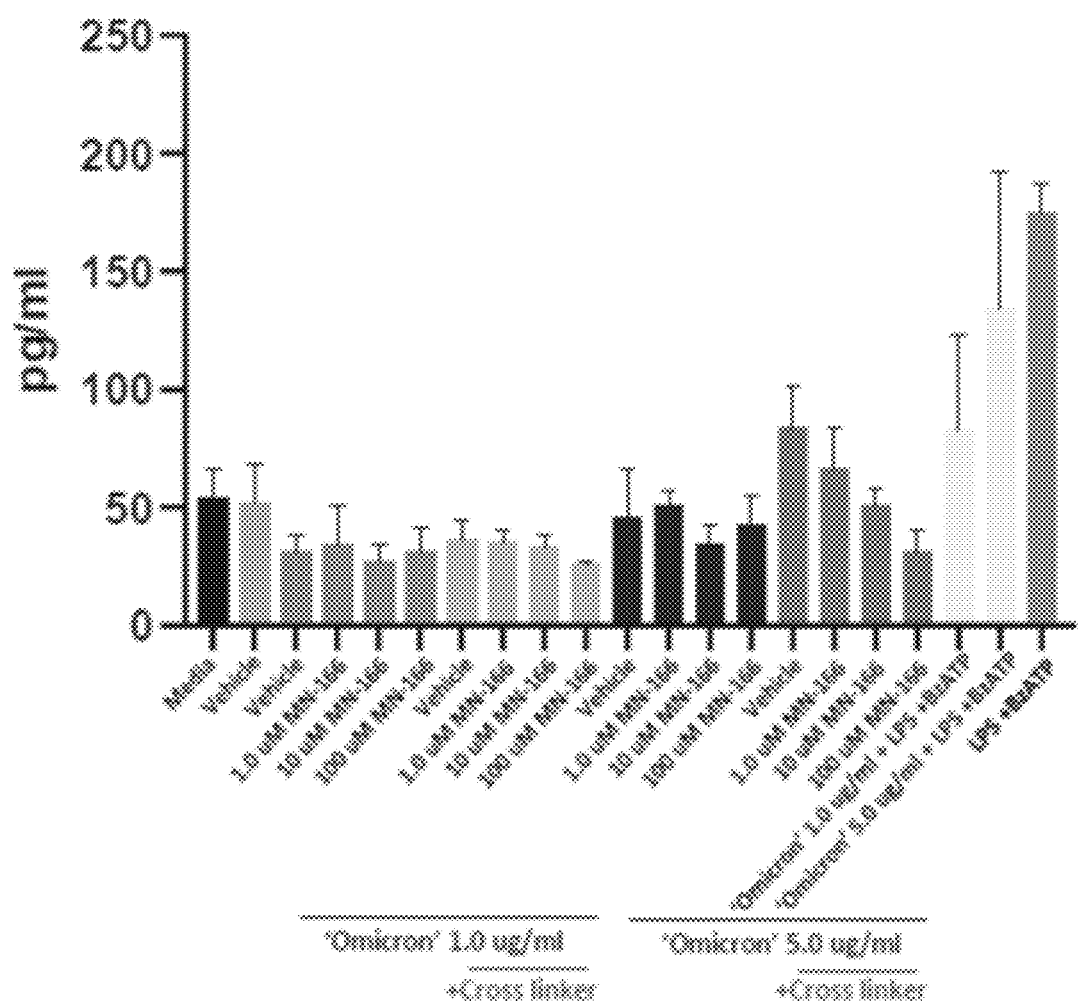

FIG. 8 depicts concentration of TNFα in the presence of media, vehicle, "Omicron" spike protein with vehicle, "Omicron" spike protein (1.0 µg/ml) with ibudilast (at 1, 10, or 100 µM), "Omicron" spike protein (1.0 µg/ml) with cross-linker and ibudilast (at 1, 10, or 100 µM), "Omicron" spike protein (5.0 µg/ml) with ibudilast (at 1, 10, or 100 µM), "Omicron" spike protein (5.0 µg/ml) with cross-linker and ibudilast (at 1, 10, or 100 µM), "Omicron" spike protein (1.0 µg/ml) with LPS and BzATP, "Omicron" spike protein (5.0 µg/ml) with LPS and BzATP, and LPS and BzATP using cells from donor 3.

DETAILED DESCRIPTION

The practice of the present disclosure will employ, unless otherwise indicated, conventional methods of chemistry, biochemistry, and pharmacology, within the skill of the art. Such techniques are explained fully in the literature. See, e.g.; A. L. Lehninger, Biochemistry (Worth Publishers, Inc., current addition); Morrison and Boyd, Organic Chemistry (Allyn and Bacon, Inc., current addition); J. March, Advanced Organic Chemistry (McGraw Hill, current addition); Remington: The Science and Practice of Pharmacy, A. Gennaro, Ed., 20th Ed.; FDA's Orange Book, Goodman & Gilman The Pharmacological Basis of Therapeutics, J. Griffith Hardman, L. L. Limbird, A. Gilman, 11th Ed., 2005, The Merck Manual, 18th edition, 2007, and The Merck Manual of Medical Information 2003.

All publications cited herein, including internet articles, the FDA Orange Book (available on the FDA's website), books, handbooks, journal articles, patents and patent applications, whether supra or infra, are hereby incorporated by reference in their entirety.

Definitions

Before describing the present disclosure in detail, it is to be understood that this disclosure is not limited to particular administration modes, patient populations, and the like, as such may vary, as will be apparent from the accompanying description.

It must be noted that, as used in this specification and the intended claims, the singular forms "a," "an," and "the" include plural referents unless the context clearly dictates otherwise. Thus, for example, reference to "a drug" includes a single drug as well as two or more of the same or different drugs, reference to "an optional excipient" refers to a single optional excipient as well as two or more of the same or different optional excipients, and the like.

In describing and claiming the present disclosure, the following terminology will be used in accordance with the definitions described below.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention. When an embodiment is defined by one of these terms (e.g., "comprising") it should be understood that this disclosure also includes alternative embodiments, such as "consisting essentially of" and "consisting of" for said embodiment.

"Pharmaceutically acceptable excipient or carrier" refers to an excipient that may optionally be included in the compositions of the disclosure and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium).

"Active molecule" or "active agent" as described herein includes any agent, drug, compound, composition of matter or mixture which provides some pharmacologic, often beneficial, effect that can be demonstrated in-vivo or in vitro. This includes foods, food supplements, nutrients, nutraceuticals, drugs, vaccines, antibodies, vitamins, and other beneficial agents. As used herein, the terms further include any physiologically or pharmacologically active substance that produces a localized or systemic effect in a patient. In specific embodiments, the active molecule or active agent may include ibudilast or a pharmaceutically acceptable salt thereof.

"Substantially" or "essentially" means nearly totally or completely, for instance, 95% or greater of some given quantity.

"Optional" or "optionally" means that the subsequently described circumstance may or may not occur, so that the description includes instances where the circumstance occurs and instances where it does not.

The terms "subject," "individual" or "patient" are used interchangeably herein and refer to a vertebrate, preferably a mammal. Mammals include, but are not limited to, mice, rodents, rats, simians, humans, farm animals, dogs, cats, sport animals, and pets.

The terms "pharmacologically effective amount" or "therapeutically effective amount" of a composition or agent, as provided herein, refer to a nontoxic but sufficient amount of the composition or agent to provide the desired response, such as a reduction or recovery from post-acute sequelae of SARS-COV-2. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

The term "about," will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term. For example, in some embodiments, it will mean plus or minus 5% of the particular term. Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number.

As used herein, the term "post-COVID condition(s)" or "long COVID" or "post-COVID syndrome" or "post-acute sequelae of SARS-COV-2" refers to one or more of new, returning, or ongoing symptom(s) that can last weeks or months after initial infection with the virus that causes COVID-19. Non-limiting examples of such symptoms include anxiety, general pain or discomfort, fatigue, insomnia, cognitive impairment (e.g., memory lapse and impaired concentration), depression, shortness of breath, post-traumatic stress disorder, joint pain, muscle pain, chest pain or tightness, palpitations, smell or taste dysfunction, sleep difficulties, hair loss, and rash.

As used herein, the term "treatment" or "treating" means any treatment of a condition or associated disorder, in a patient, including inhibiting the condition or associated disorder, that is, arresting or suppressing the development of clinical symptoms, such as anxiety, general pain or discomfort, fatigue, insomnia, cognitive impairment, depression, shortness of breath, post-traumatic stress disorder, joint pain, muscle pain, chest pain or tightness, palpitations, smell or taste dysfunction, sleep difficulties, hair loss, and rash.

In some aspects, the term treating refers to an improvement in clinical outcomes due to delayed administration of ibudilast after infection with SARS-COV-2 and development of symptoms. The term "clinical outcome" refers to any clinical observation or measurement relating to a patient's reaction to a therapy. Non-limiting examples of clinical outcomes include clinical observation of or assessment using a Digit Symbol Substitution Test, a Trails Making Test, a Rey's auditory verbal learning test, a Fatigue Severity Scale, a 7-item Generalized Anxiety Scale, or a 5-item World Health Organization Wellbeing Scale, or any combination thereof, in the patient in reaction to the therapy.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

The methods of the disclosure are based upon administration of the molecule, ibudilast. Ibudilast is a small molecule drug (molecular weight of 230.3) having the structure shown below.

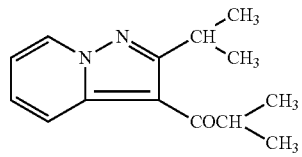

Ibudilast is also found under ChemBank ID 3227, CAS #50847 Nov. 5, and Beilstein Handbook Reference No. May 24, 2003-00396. Its molecular formula corresponds to C14H18N2O. Ibudilast is also known by various chemical names including 2-methyl-1-(2-(1-methylethyl) pyrazolo (1,5-a) pyridin-3-yl) 1-propanone; 3-isobutyryl-2-isopropylpyrazolo (1,5-a) pyridine; and 1-(2-isopropyl-pyrazolo[1,5-a]pyridin-3-yl)-2-methyl-propan-1-one. Other synonyms for ibudilast include Ibudilastum (Latin), BRN 0656579, KC-404, and MN-166. Its brand name is Ketas®. Ibudilast, as referred to herein, is meant to include any and all pharmaceutically acceptable salt forms thereof, prodrug forms (e.g., the corresponding ketal, oxime, oxime derivative, hydrazone, or semicarbazone), solvates, and the like, as appropriate for use in its intended formulation for administration.

Ibudilast is also a selective inhibitor of cyclic nucleotide phosphodiesterases (PDEs) 3A, 4, 10A1 and 11A1 (Gibson et al., Eur J Pharmacol 538:39-42, 2006) and has toll-like receptor-4 (TLR4) antagonistic activity (Yang et al., Cell Death and Disease (2016) 7, e2234; doi: 10.1038/cddis.2016.140) and has also been reported to have leukotriene D4 and PAF antagonistic activities. Its profile appears effectively anti-inflammatory and unique in comparison to other PDE inhibitors and anti-inflammatory agents. PDEs catalyze the hydrolysis of the phosphoester bond on the 3'-carbon to yield the corresponding 5'-nucleotide monophosphate. Thus, they regulate the cellular concentrations of cyclic nucleotides. Since extracellular receptors for many hormones and neurotransmitters utilize cyclic nucleotides as second messengers, the PDEs also regulate cellular responses to these extracellular signals. There are at least eight classes of PDEs: Ca2+/calmodulin-dependent PDEs (PDE1); cGMP-stimulated PDEs (PDE2); cGMP-inhibited PDEs (PDE3); cAMP-specific PDEs (PDE4); cGMP-binding PDEs (PDE5); photoreceptor PDEs (PDE6); high affinity, cAMP-specific PDEs (PDE7); and high affinity cGMP-specific PDEs (PDE9). Ibudilast acts to suppress inflammation via action on inflammatory cells (e.g., glial cells) resulting in the suppression of both pro-inflammatory mediator and neuroactive mediator release. Ibudilast may also suppress the production of pro-inflammatory cytokines (IL-1β, TNF-α) and may enhance the production of the anti-inflammatory cytokines (IL-4, IL-10). References related to the foregoing include the following: Obernolte, R., et al. (1993) "The cDNA of a human lymphocyte cyclic-AMP phosphodiesterase (PDE IV) reveals a multigene family" Gene 129:239-247; Rile, G., et al. (2001) "Potentiation of ibudilast inhibition of platelet aggregation in the presence of endothelial cells" Thromb. Res. 102:239-246; Souness, J. E., et al. (1994) "Possible role of cyclic AMP phosphodiesterases in the actions of ibudilast on eosinophil thromboxane generation and airways smooth muscle tone" Br. J. Pharmacol. 111:1081-1088; Suzumura, A., et al. (1999) "Ibudilast suppresses TNF.alpha. production by glial cells functioning mainly as type III phosphodiesterase inhibitor in CNS" Brain Res. 837:203-212; Takuma, K., et al. (2001) "Ibudilast attenuates astrocyte apoptosis via cyclic GMP signaling pathway in an in vitro reperfusion model" Br. J. Pharmacol. 133:841-848. With regards to the treatment of cancers of the CNS, ibudilast exhibits good CNS penetration. (Sanftner et al Xenobiotica 2009 39:964-977).

Ibudilast is also an allosteric inhibitor of p-hydoxyphenylpyruvate (HPP) tautomerase activity of macrophage inhibitory factor (MIF) (Cho et al., PNAS-USA, 2010 June 107:11313-8), thereby inhibiting the catalytic and chemotactic functions of MIF. It was unexpectedly found by the inventors that ibudilast also lowers plasma level of MIF. Such a decrease in MIF plasma level is unexpected since there is no known connection between allosteric inhibition of MIF and MIF concentration in plasma. However, since MIF is involved in intracellular signaling through activation of CD74 in a complex with CD44 or the chemokine receptors CXCR2 and CXCR4, both the MIF inhibition and decrease in MIF plasma level by ibudilast can minimize the proinflammatory action of MIF.

As stated previously, a reference to any one or more of the herein-described drugs, in particular ibudilast, is meant to encompass, where applicable, any and all enantiomers, mixtures of enantiomers including racemic mixtures, prodrugs, pharmaceutically acceptable salt forms, hydrates (e.g., monohydrates, dihydrates, etc.), solvates, different physical forms (e.g., crystalline solids, amorphous solids), metabolites, and the like.

Methods of Treatment and Administration

As set forth above, in one aspect, the present disclosure is directed to a methods of treating post-COVID condition(s) in a subject in need thereof, the method comprising, consisting essentially of, or consisting of administering to the subject a therapeutically effective amount of ibudilast, or a pharmaceutical salt thereof. Such administration is effective to attenuate or reverse post-COVID condition(s) in the subject. Post-COVID condition(s) comprise one or more selected from anxiety, general pain or discomfort, fatigue, insomnia, cognitive impairment, depression, shortness of breath, post-traumatic stress disorder, joint pain, muscle pain, chest pain or tightness, palpitations, smell or taste dysfunction, sleep difficulties, hair loss, and rash. In some embodiments, the post-COVID condition(s) comprises, consists essentially of, or consists of cognitive impairment.

In another aspect, a method is provided to treat cognitive impairment in a patient suffering from or diagnosed with post-COVID condition(s), the method comprising, consisting essentially of, or consisting of administering to the subject a therapeutically effective amount of ibudilast, or a pharmaceutical salt thereof.

In some embodiments, ibudilast or a pharmaceutically acceptable salt thereof is administered at a daily dosage amount ranging from about 0.1 mg to 720 mg daily, from about 30 mg to 200 mg daily, from about 60 mg to 600 mg daily, or from about 100 mg to 480 mg daily. Additional dosage amounts are discussed below.

Ibudilast administration may be accomplished through various modes of delivery of ibudilast comprising formulations. Preferred methods of delivery of ibudilast-based therapeutic formulations include systemic and localized delivery. Such routes of administration include but are not limited to, oral, intra-arterial, intrathecal, intraspinal, intramuscular, intraperitoneal, intranasal, and inhalation routes.

More particularly, an ibudilast-based formulation may be administered for therapy by any suitable route, including without limitation, oral, rectal, nasal (including inhalation), topical (including transdermal, aerosol, buccal and sublingual), vaginal, parenteral (including subcutaneous, intravenous, intramuscular, and intradermal), intrathecal, and pulmonary. In some embodiments, the ibudilast-based formulation is administered orally. In some embodiments, the ibudilast-based formulation is administered through an injection. The preferred route will, of course, vary with the condition and age of the recipient, the particular syndrome being treated, and the specific combination of drugs employed.

In some embodiments, the ibudilast or pharmaceutically acceptable salt thereof is administered orally. In some embodiments, the ibudilast or pharmaceutically acceptable salt thereof is administered through an injection.

An ibudilast composition, when comprising more than one active agent, may be administered as a single combination composition comprising a combination of ibudilast and at least one additional active agent. In terms of patient compliance and ease of administration, such an approach is preferred, since patients are often averse to taking multiple pills or dosage forms, often multiple times daily, over the duration of treatment. Alternatively, the combination of the disclosure is administered as separate dosage forms. In instances in which the drugs comprising the therapeutic composition of the disclosure are administered as separate dosage forms and co-administration is required, ibudilast and each of the additional active agents may be administered simultaneously, sequentially in any order, or separately.

Dosages

Therapeutic amounts can be empirically determined and will vary with the particular condition being treated, the subject, and the efficacy and toxicity of each of the active agents contained in the composition. The actual dose to be administered will vary depending upon the age, weight, and general condition of the subject as well as the severity of the condition being treated, the judgment of the health care professional, and particular combination being administered.

Therapeutically effective amounts may be adjusted to the requirements of each particular case. Generally, a therapeutically effective amount of ibudilast or pharmaceutically acceptable salt thereof will range from a total daily dosage of about 0.1 mg/day to 720 mg/day, about 40-600 mg/day, or about 100-480 mg/day, or more preferably, in an amount between about 1-240 mg/day, about 30-240 mg/day, about 30-200 mg/day, about 30-120 mg/day, about 1-120 mg/day, about 50-150 mg/day, about 60-150 mg/day, about 60-120 mg/day, or about 60-100 mg/day, administered as either a single dosage or as multiple dosages. In some embodiments, the therapeutically effective amount of ibudilast or pharmaceutically acceptable salt thereof is from about 30-200 mg/day, administered as either a single dosage or as multiple dosages. In some embodiments, multiple dosages include two, three, or four doses per day.

Preferred dosage amounts include dosages greater than about 20 mg BID or TID. That is to say, a preferred dosage amount is greater than about 30 mg/day, 60 mg/day, 90 mg/day, 120 mg/day, 150 mg/day, 180 mg/day, 210 mg/day, 240 mg/day, 270 mg/day, 300 mg/day, 360 mg/day, 400 mg/day, 440 mg/day, 480 mg/day, 520 mg/day, 580 mg/day, 600 mg/day, 620 mg/day, 640 mg/day, 680 mg/day, and 720 mg/day or more.

In some embodiments, the therapeutically effective amount of ibudilast or pharmaceutically acceptable salt thereof is at least 30 mg/day, at least 40 mg/day, at least 50 mg/day, at least 60 mg/day, at least 70 mg/day, at least 80 mg/day, at least 90 mg/day, at least 100 mg/day, at least 110 mg/day, at least 120 mg/day, at least 130 mg/day, at least 140 mg/day, at least 150 mg/day, at least 160 mg/day, at least 170 mg/day, at least 180 mg/day, at least 190 mg/day, at least 200 mg/day, at least 225 mg/day, at least 250 mg/day, at least 275 mg/day, at least 300 mg/day, at least 325 mg/day, at least 350 mg/day, at least 375 mg/day, at least 400 mg/day, at least 425 mg/day, at least 450 mg/day, at least 475 mg/day, at least 500 mg/day, at least 525 mg/day, at least 550 mg/day, at least 575 mg/day, at least 600 mg/day, at least 625 mg/day, at least 650 mg/day, at least 675 mg/day, at least 700 mg/day, or at least 720 mg/day. In some embodiments, the therapeutically effective amount of ibudilast or pharmaceutically acceptable salt thereof is at least 60 mg/day. In some embodiments, the therapeutically effective amount of ibudilast or pharmaceutically acceptable salt thereof is at least 100 mg/day.

Depending upon the dosage amount and precise condition to be treated, administration can be one, two, three, or four times daily for a time course of one day to several days, weeks, months, and even years, and may even be for the life of the patient. Illustrative dosing regimens will last a period of at least about a week, from about 1-4 weeks, from 1-3 months, from 1-6 months, from 1-52 weeks, from 1-24 months, or longer. In some embodiments, the ibudilast or the pharmaceutically acceptable salt thereof is administered for 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days. In some embodiments, the ibudilast or the pharmaceutically acceptable salt thereof is administered for two months or less. In some embodiments, the ibudilast or the pharmaceutically acceptable salt thereof is administered for at least two months. In some embodiments, the ibudilast or the pharmaceutically acceptable salt thereof is administered for at least six months. In some embodiments, the ibudilast or the pharmaceutically acceptable salt thereof is administered for 1, 2, 3, 4, 5, 6, 7, 8, 9, 10, 11, or 12 months, or more. In some embodiments, the ibudilast or the pharmaceutically acceptable salt thereof is administered for about 1, 2, 3, 4, 5, 6, 7, 8, 9, or 10 years, or more. In some embodiments, the ibudilast or the pharmaceutically acceptable salt thereof is administered for at least 1 year. In some embodiments, the ibudilast or the pharmaceutically acceptable salt thereof is administered for at least 2 years. In some embodiments, the ibudilast or the pharmaceutically acceptable salt thereof is administered as a one-time single dose.

In some embodiments, the therapeutically effective amount of ibudilast or the pharmaceutically acceptable salt thereof is administered in a single dosage per day. In some embodiments, the therapeutically effective amount of ibudilast or the pharmaceutically acceptable salt thereof is administered in two dosages per day. In some embodiments, the therapeutically effective amount of ibudilast or the pharmaceutically acceptable salt thereof is administered in three dosages per day. In some embodiments, the therapeutically effective amount of ibudilast or the pharmaceutically acceptable salt thereof is administered in four dosages per day. In some embodiments, the therapeutically effective amount of ibudilast or the pharmaceutically acceptable salt thereof is administered continually.

In some embodiments, the ibudilast or pharmaceutically acceptable salt thereof is administered at least once daily. In some embodiments, the ibudilast or pharmaceutically acceptable salt thereof is administered at least twice daily. In some embodiments, the ibudilast or the pharmaceutically acceptable salt thereof is administered once daily. In some embodiments, the ibudilast or pharmaceutically acceptable salt thereof is administered twice daily.

Practically speaking, a unit dose of any given composition of the disclosure or active agent can be administered in a variety of dosing schedules, depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, every other day, three times weekly, twice weekly, once weekly, twice monthly, once monthly, and so forth.

Formulations

Ibudilast may be administered in a composition of formulation which may optionally contain one or more additional components as described below.

Excipients/Carriers

In addition to ibudilast or a pharmaceutically acceptable salt thereof, the compositions of the disclosure may further comprise one or more pharmaceutically acceptable excipients or carriers. Exemplary excipients include, without limitation, polyethylene glycol (PEG), PEG 400, (2-Hydroxypropyl)-B-cyclodextrin, hydrogenated castor oil (HCO), cremophors, carbohydrates, starches (e.g., corn starch), inorganic salts, antimicrobial agents, antioxidants, binders/fillers, surfactants, lubricants (e.g., calcium or magnesium stearate), glidants such as talc, disintegrants, diluents, buffers, acids, bases, film coats, combinations thereof, and the like.

A composition of the disclosure may include one or more carbohydrates such as a sugar, a derivatized sugar such as an alditol, aldonic acid, an esterified sugar, and/or a sugar polymer. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

Also suitable for use in the compositions of the disclosure are potato and corn-based starches such as sodium starch glycolate and directly compressible modified starch.

Further, representative excipients include inorganic salt or buffers such as citric acid, sodium chloride, potassium chloride, sodium sulfate, potassium nitrate, sodium phosphate monobasic, sodium phosphate dibasic, and combinations thereof.

A composition of the disclosure may also contain one or more antioxidants. Antioxidants are used to prevent oxidation, thereby preventing the deterioration of the drug(s) or other components of the preparation. Suitable antioxidants for use in the present disclosure include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

Additional exemplary excipients include surfactants such as polysorbates, e.g., "Tween 20" and "Tween 80," and pluronics such as F68 and F88 (both of which are available from BASF, Mount Olive, N.J.), sorbitan esters, lipids (e.g., phospholipids such as lecithin and other phosphatidylcholines, and phosphatidylethanolamines), fatty acids and fatty esters, steroids such as cholesterol, and chelating agents, such as EDTA, zinc and other such suitable cations. In some embodiments, the surfactant may comprise polyethoxylated castor oil derivatives (e.g., Cremophor EL, Kolliphor ELP, and the like). Other non-limiting excipients include alcohol (e.g., ethanol), propylene glycol, glyderol, or polyethyleneglycol (PEG).

Further, a composition of the disclosure may optionally include one or more acids or bases. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Non-limiting examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumarate, and combinations thereof.

The amount of any individual excipient in the composition will vary depending on the role of the excipient, the dosage requirements of the active agent components, and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5% to about 98% by weight, more preferably from about 15% to about 95% by weight of the excipient. In general, the amount of excipient present in an ibudilast composition of the disclosure is selected from the following: at least about 2%, 5%, 10%, 15%, 20%, 25%, 30%, 35%, 40%, 45%, 50%, 55%, 60%, 65%, 70%, 75%, 80%, 85%, 90%, or even 95% by weight.

These foregoing pharmaceutical excipients along with other excipients are described in "Remington: The Science & Practice of Pharmacy", 19th ed., Williams & Williams, (1995), the "Physician's Desk Reference", 52.sup.nd ed., Medical Economics, Montvale, N.J. (1998), and Kibbe, A. H., Handbook of Pharmaceutical Excipients, 3.sup.rd Edition, American Pharmaceutical Association, Washington, D.C., 2000.

Other Actives

A formulation (or kit) in accordance with the disclosure may contain, in addition to ibudilast or a pharmaceutically acceptable salt thereof, one or more other therapeutic active agents.

Preferably, the one or more other therapeutic agent is one that possesses a mechanism of action different from that of ibudilast. Such active ingredients can be found listed in the FDA's Orange Book, Goodman & Gilman The Pharmacological Basis of Therapeutics, J. Griffith Hardman, L. L. Limbird, A. Gilman, 11th Ed., 2005, The Merck Manual, 18th edition, 2007, and The Merck Manual of Medical Information 2003.

In some embodiments, the one or more other therapeutic active agents are a corticosteroid, a COX-2 (cyclooxygenase-2) inhibitor, a NSAID (non-steroidal anti-inflammatory drug), a SSRI (selective serotonin reuptake inhibitor), a SNRI (serotonin and norepinephrine reuptake inhibitor), a tricyclic antidepressant, an antihistamine, a beta-blocker, cannabidiol, ATP (adenosine triphosphate), ifenprodil tartrate, neurotropin, gabapentin, pregabalin, mirtazapine, or a combination of two or more thereof In some embodiments, the one or more other therapeutic active agents are one or more corticosteroids. Non-limiting examples of corticosteroids include cortisone, prednisone, prednisolone, methylprednisolone, dexamethasone, betamethasone, hydrocortisone, amcinonide, budesonide, desonide, fluocinolone acetonide, fluocinonide, halcinonide, triamcinolone acetonide, beclometasone, fluocortolone, halometasone, mometasone, alclometasone dipropionate, betamethasone dipropionate, betamethasone valerate, clobetasol propionate, clobetasone butyrate, fluprednidene acetate, and mometasone furoate.

In some embodiments, the one or more other therapeutic active agents are one or more NSAIDs. Non-limiting examples of NSAIDs include ibuprofen, naproxen, diclofenac, mefenamic acid, etoricoxib, indomethacin, and aspirin (e.g., high-dose aspirin).

In some embodiments, the one or more other therapeutic active agents are one or more COX-2 inhibitors. Non-limiting examples of COX-2 inhibitors include celecoxib, rofecoxib, and valdecoxib.

In some embodiments, the one or more other therapeutic active agents are one or more SSRIs. Non-limiting examples of SSRIs include citalopram, escitalopram, fluoxetine, paroxetine, dapoxetine, vortioxetine, fluvoxamine, and sertraline.

In some embodiments, the one or more other therapeutic active agents are one or more SNRIs. Non-limiting examples of SNRIs include desvenlafaxine, duloxetine, venlafaxine, and levomilnacipran.

In some embodiments, the one or more other therapeutic active agents are one or more tricyclic antidepressants. Non-limiting examples of tricyclic antidepressants include amitriptyline, amoxapine, desipramine, doxepin, imipramine, nortriptyline, protriptyline, and trimipramine.

In some embodiments, the one or more other therapeutic active agents are one or more antihistamines. Non-limiting examples of antihistamines include diphenhydramine, cetirizine, chlorpheniramine, cyclizine, dimenhydrinate, doxylamine, hydroxyzine, meclizine, carbinoxamine, cyproheptadine, desloratadine, emedastine, levocetirizine brompheniramine. clemastine, fexofenadine, and loratadine.

In some embodiments, the one or more other therapeutic active agents are one or more beta blockers. Non-limiting examples of beta blockers include atenolol, betaxolol, bisoprolol, esmolol, acebutolol, metoprolol tartrate, metoprolol succinate, and nebivolol.

The dosage amounts provided above are meant to be merely guidelines; the precise amount of a secondary active agent to be administered during combination therapy with ibudilast or the pharmaceutically acceptable salt thereof will, of course, be adjusted accordingly and will depend upon factors such as intended patient population, the particular symptom or condition to be treated, potential synergies between the active agents administered, and the like, and will readily be determined by one skilled in the art based upon the guidance provided herein.

Sustained Delivery Formulations

Preferably, the compositions are formulated in order to improve stability and extend the half-life of ibudilast or the pharmaceutically acceptable salt thereof. For example, ibudilast or the pharmaceutically acceptable salt thereof may be delivered in a controlled or extended-release formulation. Controlled or extended-release formulations are prepared by incorporating ibudilast or the pharmaceutically acceptable salt thereof into a carrier or vehicle such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. Additionally, ibudilast or the pharmaceutically acceptable salt thereof can be encapsulated, adsorbed to, or associated with, particulate carriers. Examples of particulate carriers include those derived from polymethyl methacrylate polymers, as well as microparticles derived from poly (lactides) and poly (lactide-co-glycolides), known as PLG. See, e.g., Jeffery et al., Pharm. Res. (1993) 10:362-368; and McGee et al., J. Microencap. (1996).

Extended release polymers suitable for this purpose are known in the art and include hydrophobic polymers such as cellulose ethers. Non-limiting examples of suitable cellulose ethers include ethyl cellulose, cellulose acetate and the like; polyvinyl esters such as polyvinyl acetate, polyacrylic acid esters, methacrylic and acrylate polymers (pH-independent types); high molecular weight polyvinyl alcohols and waxes such as fatty acids and glycerides, methacrylic acid ester neutral polymers, polyvinyl alcohol-maleic anhydride copolymers and the like; ethylacrylate-methylmethacrylate copolymers; aminoalkyl methacrylate copolymers; and mixtures thereof.

Delivery Forms

The ibudilast or pharmaceutically acceptable salt thereof compositions described herein encompass all types of formulations, and in particular, those that are suited for systemic or intrathecal administration. Oral dosage forms include tablets, lozenges, capsules, syrups, oral suspensions, emulsions, granules, and pellets. In some embodiments, the oral dosage form is a tablet. In some embodiments, the tablet is an extended release tablet. In some embodiments, the oral dosage form is a capsule. In some embodiments, the capsule is an extended release capsule.

Alternative formulations include aerosols, transdermal patches, gels, creams, ointments, suppositories, powders or lyophilates that can be reconstituted, as well as liquids. Examples of suitable diluents for reconstituting solid compositions, e.g., prior to injection, include bacteriostatic water for injection, dextrose 5% in water, phosphate-buffered saline, Ringer's solution, saline, sterile water, deionized water, and combinations thereof. With respect to liquid pharmaceutical compositions, solutions and suspensions are envisioned. Preferably, an ibudilast or pharmaceutically acceptable salt thereof composition of the disclosure is one suited for oral administration.

In turning now to oral delivery formulations, tablets can be made by compression or molding, optionally with one or more accessory ingredients or additives. Compressed tablets are prepared, for example, by compressing in a suitable tabletting machine, the active ingredients in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) and/or surface-active or dispersing agent.

Molded tablets are made, for example, by molding in a suitable tabletting machine, a mixture of powdered compounds moistened with an inert liquid diluent. The tablets may optionally be coated or scored, and may be formulated so as to provide slow or controlled release of the active ingredients, using, for example, hydroxypropylmethyl cellulose in varying proportions to provide the desired release profile. Tablets may optionally be provided with a coating, such as a thin film, sugar coating, or an enteric coating to provide release in parts of the gut other than the stomach. Processes, equipment, and toll manufacturers for tablet and capsule making are well-known in the art.

Formulations for topical administration in the mouth include lozenges comprising the active ingredients, generally in a flavored base such as sucrose and acacia or tragacanth and pastilles comprising the active ingredients in an inert base such as gelatin and glycerin or sucrose and acacia.

A pharmaceutical composition for topical administration may also be formulated as an ointment, cream, suspension, lotion, powder, solution, paste, gel, spray, aerosol or oil.

Alternatively, the formulation may be in the form of a patch (e.g., a transdermal patch) or a dressing such as a bandage or adhesive plaster impregnated with active ingredients and optionally one or more excipients or diluents. Topical formulations may additionally include a compound that enhances absorption or penetration of the ingredients through the skin or other affected areas, such as dimethylsulfoxidem bisabolol, oleic acid, isopropyl myristate, and D-limonene, to name a few.

For emulsions, the oily phase is constituted from known ingredients in a known manner. While this phase may comprise merely an emulsifier (otherwise known as an emulgent), it desirably comprises a mixture of at least one emulsifier with a fat and/or an oil. Preferably, a hydrophilic emulsifier is included together with a lipophilic emulsifier that acts as a stabilizer. Together, the emulsifier(s) with or without stabilizer(s) make up the so-called emulsifying wax, and the wax together with the oil and/or fat make up the so-called emulsifying ointment base which forms the oily dispersed phase of cream formulations. Illustrative emulgents and emulsion stabilizers include Tween 60, Span 80, cetostearyl alcohol, myristyl alcohol, glyceryl monostearate and sodium lauryl sulfate.

Formulations for rectal administration are typically in the form of a suppository with a suitable base comprising, for example, cocoa butter or a salicylate.

Formulations suitable for vaginal administration generally take the form of a suppository, tampon, cream, gel, paste, foam, or spray.

Formulations suitable for nasal administration, wherein the carrier is a solid, include a coarse powder having a particle size, for example, in the range of about 20 to about 500 microns. Such a formulation is typically administered by rapid inhalation through the nasal passage, e.g., from a container of the powder held in proximity to the nose. Alternatively, a formulation for nasal delivery may be in the form of a liquid, e.g., a nasal spray or nasal drops.

Aerosolizable formulations for inhalation may be in dry powder form (e.g., suitable for administration by a dry powder inhaler), or, alternatively, may be in liquid form, e.g., for use in a nebulizer. Nebulizers for delivering an aerosolized solution include the AERx® (Aradigm), the Ultravent® (Mallinkrodt), and the Acorn II® (Marquest Medical Products). A composition of the disclosure may also be delivered using a pressurized, metered dose inhaler (MDI), e.g., the Ventolin® metered dose inhaler, containing a solution or suspension of a combination of drugs as described herein in a pharmaceutically inert liquid propellant, e.g., a chlorofluorocarbon or fluorocarbon.

Formulations suitable for parenteral administration include aqueous and non-aqueous isotonic sterile solutions suitable for injection, as well as aqueous and non-aqueous sterile suspensions.

Parenteral formulations of the disclosure are optionally contained in unit-dose or multi-dose sealed containers, for example, ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules, and tablets of the types previously described.

A formulation of the disclosure may also be an extended release formulation, such that each of the drug components is released or absorbed slowly over time, when compared to a non-sustained release formulation. Sustained release formulations may employ pro-drug forms of the active agent, delayed-release drug delivery systems such as liposomes or polymer matrices, hydrogels, or covalent attachment of a polymer such as polyethylene glycol to the active agent.

In addition to the ingredients particularly mentioned above, the formulations of the disclosure may optionally include other agents conventional in the pharmaceutical arts and particular type of formulation being employed, for example, for oral administration forms, the composition for oral administration may also include additional agents as sweeteners, thickeners or flavoring agents.

Kits

Also provided herein is a kit containing at least one composition of the disclosure, accompanied by instructions for use.

In some embodiments, the kit contains at least one combination composition described herein, accompanied by instructions for use. For example, in instances in which each of the drugs themselves are administered as individual or separate dosage forms, the kit comprises ibudilast in addition to each of the drugs making up the composition of the disclosure, along with instructions for use. The drug components may be packaged in any manner suitable for administration, so long as the packaging, when considered along with the instructions for administration, clearly indicates the manner in which each of the drug components is to be administered.

For example, for an illustrative kit comprising ibudilast and one other active agent, the kit may be organized by any appropriate time period, such as by day. As an example, for Day 1, a representative kit may comprise unit dosages of each of ibudilast and the one other active agent. If each of the drugs is to be administered twice daily, then the kit may contain, corresponding to Day 1, two rows of unit dosage forms of each of ibudilast and the one other active agent, along with instructions for the timing of administration. Alternatively, if one or more of the drugs differs in the timing or quantity of unit dosage form to be administered in comparison to the other drug members of the combination, then such would be reflected in the packaging and instructions. Various embodiments according to the above may be readily envisioned, and would of course depend upon the particular combination of drugs, in addition to ibudilast, employed for treatment, their corresponding dosage forms, recommended dosages, intended patient population, and the like. The packaging may be in any form commonly employed for the packaging of pharmaceuticals, and may utilize any of a number of features such as different colors, wrapping, tamper-resistant packaging, blister packs, desiccants, and the like.

It is to be understood that while the disclosure has been described in conjunction with preferred specific embodiments, the foregoing description as well as the examples that follow are intended to illustrate and not limit the scope of the disclosure. Other aspects, advantages and modifications within the scope of the disclosure will be apparent to those skilled in the art to which the disclosure pertains.

All references mentioned in this application, including any patents, published patent applications, books, handbooks, journal publications, or the FDA Orange Book are hereby incorporated by reference herein, in their entirety.

The following examples are given for the purpose of illustrating various embodiments of the disclosure and are not meant to limit the present disclosure in any fashion. One skilled in the art will appreciate readily that the present disclosure is well adapted to carry out the objects and obtain the ends and advantages mentioned, as well as those objects, ends and advantages inherent herein. The present examples, along with the methods described herein are presently representative of embodiments and are exemplary, and are not intended as limitations on the scope of the disclosure. Changes therein and other uses which are encompassed within the spirit of the disclosure as defined by the scope of the claims will occur to those skilled in the art.

EXAMPLES

Example 1: Post-COVID Syndrome Pilot Study

A pilot study is conducted with an enrollment goal of 20-40 patients (female or male; 18 years or older; having a medical history of confirmed COVID-19 with sequela symptoms for more than 6 weeks). Patients are orally administered ibudilast capsules, 20 mg to 30 mg b.i.d. or matching placebo capsules b.i.d. for 8 weeks. Efficacy endpoints are assessed by one or more of the following:

Post COVID-19 Functional Status (PCFS) scale
Fatigue Severity scale (FSS)
Digital Symbol Substitution Test (DSST)
Health-related quality of life questionnaire (SF-36 Questionnaire)
Perceived Deficits Questionnaire, 20-item (PDQ-20)
Trail Making Test Part A and B
Serum biomarker (e.g., inflammatory cytokine level)

Example 2: Multi-Site Clinical Trial

A multi-arm open-label, pragmatic, adaptive randomized controlled trial of 800-1000 patients age >16 who have confirmed COVID-19 and have had lingering symptoms for greater than 3 months is conducted. A run-in period of 4-8 weeks is to be used where standard of care therapies are to be initiated. Adaptive randomization allows for real-time testing of various interventions. More participants are to be randomized to the more effective intervention, while frequent interim analyses will facilitate the discontinuation of interventions when futility criteria have been met, allowing new interventions to be introduced and tested. Interventions are to last for 4 weeks and all participants are to be followed for 8 weeks after completion of therapy. This trial is to have 3 intervention arms and a standard of care arm. An interdisciplinary science committee will determine and prioritize interventions to be tested based on evolving evidence. Symptoms such as anxiety, general pain or discomfort, fatigue, insomnia, cognitive impairment, depression, shortness of breath, post-traumatic stress disorder, joint pain, muscle pain, chest pain or tightness, palpitations, smell or taste dysfunction, sleep difficulties, hair loss, and rash are to be assessed. Primary outcome is to be assessed using the validated Post-COVID-19 Functional Status scale (PCFS) (for symptoms such as anxiety and general pain or discomfort). Secondary outcomes are assessed by symptom checklists with bothersome scale, De Paul Symptom Questionnaire 2, health-related quality of life (SF36) (for symptoms such as fatigue, insomnia, cognitive impairment, shortness of breath, joint pain, muscle pain, chest pain or tightness, palpitations, smell or taste dysfunction, and sleep difficulties), 6 minute walk test, and re-integration to normal living. Rash and hair loss are to be evaluated by regular physical assessment. Post-traumatic disorder is to be evaluated by medical history and interval medical history during the trial.

Example 3: Effect of Ibudilast on Spike Protein-Mediated Cytokine Release from Human Monocyte-Derived Microglia Peripheral blood mononuclear cells (PBMCs) were isolated from three healthy donors. Monocytes were purified from the PBMC population, plated in 96-well plates and differentiated into microglia (iMDM) with the addition of cytokines; M-CSF, GM-CSF, NGF-β, CCL2 and IL-34 for 5 days at 37° C.

iMDM were pre-incubated with vehicle control (DMSO, 0.1%) or ibudilast (1.0, 10, 100 μM) for 30 minutes prior to the addition of recombinant SARS-COV-2 spike protein ('original [Wuhan]' (Acro Biosystems SPN C52H9), 'Delta' [B.1.617.2] (Acro Biosystems SPN-C52He), 'Omicron' [B.1.1.529] (Acro Biosystems SPD-C522e); (1.0 or 5.0 μg/mL) in the absence or presence of cross-linker (anti-6X His tag antibody, Abcam; ab18184), and cultured for a further 6 or 20 h. Positive control stimulation was also performed by the addition of LPS (10, 100 ng/mL) for 6 or 20 h, and where indicated, BzATP (100 μM) stimulation for the final two hours of the culture period.

After 6 and 20 h, the cell culture supernatants were collected and stored at −20° C. for subsequent quantification of the levels of IL-6 and TNFα, both of which are inflammatory cytokines. Because inflammatory cytokines, particularly IL-6 and TNF-α are known to be associated with long COVID (Schultheiß et al. Cell Rep. Med., 2022 Jun. 21, 3 (6): 100663), the reduction of these cytokine levels by ibudilast would suggest the improvement of clinical symptoms caused by elevated IL-6 and TNF-c. Results are shown in FIGS. 1-8.

Stimulation with only the SARS spike protein did not trigger cytokine release. Addition of LPS evoked cytokine release. Ibudilast was observed to reduce IL-6 and TNFα levels when a "low" concentration (10 ng/mL) of LPS was added with the spike proteins (all variants).

The combination of spike protein and LPS elevated TNFα levels in all donors. Ibudilast reduced the (LPS+spike protein)-evoked levels of TNFα in all donors. See FIGS. 1-3.

The combination of spike protein and LPS elevated IL-6 levels in donors 2 and 3. Ibudilast reduced the (LPS+spike protein)-evoked levels of IL-6 in donors 2 and 3. In donor 1, LPS alone enhanced IL-6 release significantly, and additional spike proteins did not enhance IL-6 release further. See FIGS. 4-5.

Using the "Omicron" spike protein, elevation in TNFα levels and their reduction by ibudilast was evident under certain test conditions. See FIGS. 6-8. Dose-dependent curves are observed under the conditions of "Omicron" spike protein (1.0 μg/ml) with cross-linker and ibudilast (at 1, 10, or 100 μM) for all 3 donors, and under the conditions of "Omicron" spike protein (5.0 μg/ml) with cross-linker and ibudilast (at 1, 10, or 100 μM) for donor 3.

Certain Embodiments

Embodiment 1. A method of treating post-COVID condition(s) in a patient in need thereof, the method comprising administering to the patient a therapeutically effective amount of ibudilast, or a pharmaceutical salt thereof.

Embodiment 2. The method of Embodiment 1, wherein the post-COVID condition(s) comprise one or more selected from anxiety, general pain or discomfort, fatigue, insomnia, cognitive impairment, depression, shortness of breath, post-traumatic stress disorder, joint pain, muscle pain, chest pain or tightness, palpitations, smell or taste dysfunction, sleep difficulties, hair loss, and rash.

Embodiment 3. The method of Embodiment 2, wherein the post-COVID condition(s) comprises cognitive impairment and the cognitive impairment includes one or both of memory lapse and impaired concentration.

Embodiment 4. The method of any one of Embodiments 1-3, wherein ibudilast, or the pharmaceutically acceptable salt thereof, is administered orally.

Embodiment 5. The method of any one of Embodiments 1-3, wherein ibudilast, or the pharmaceutically acceptable salt thereof, is administered intravenously.

Embodiment 6. The method of any one of Embodiments 1-3, wherein ibudilast, or the pharmaceutically acceptable salt thereof, is administered by subcutaneous injection.

Embodiment 7. The method of any one of Embodiments 1-3, wherein ibudilast, or the pharmaceutically acceptable salt thereof, is administered by intramuscular injection.

Embodiment 8. The method of any one of Embodiments 1-3, wherein ibudilast, or the pharmaceutically acceptable salt thereof, is administered by inhalation.

Embodiment 9. The method of any one of Embodiments 1-8, wherein ibudilast, or the pharmaceutically acceptable salt thereof, is administered for 1, 2, 3, 4, 5, 6, 7, 8, 9, or 10 days, or more.

Embodiment 10. The method of any one of Embodiments 1-8, wherein ibudilast, or the pharmaceutically acceptable salt thereof, is administered for at least 2 months.

Embodiment 11. The method of any one of Embodiments 1-10, wherein ibudilast, or the pharmaceutically acceptable salt thereof, is administered at least once daily.

Embodiment 12. The method of any one of Embodiments 1-10, wherein ibudilast, or the pharmaceutically acceptable salt thereof, is administered twice daily.

Embodiment 13. The method of any one of Embodiments 1-12, wherein the therapeutically effective amount of ibudilast, or the pharmaceutically acceptable salt thereof, is from 0.1 mg to 720 mg per day.

Embodiment 14. The method of any one of Embodiments 1-12, wherein the therapeutically effective amount of ibudilast, or the pharmaceutically acceptable salt thereof, is at least 30 mg/day.

Embodiment 15. The method of any one of Embodiments 1-12, wherein the therapeutically effective amount of ibudilast, or the pharmaceutically acceptable salt thereof, is from 30 mg to 200 mg per day.

Embodiment 16. The method of any one of Embodiments 1-12, wherein the therapeutically effective amount of ibudilast, or the pharmaceutically acceptable salt thereof, is 60 mg to 600 mg daily.

Embodiment 17. The method of any one of Embodiments 1-12, wherein the therapeutically effective amount of ibudilast, or the pharmaceutically acceptable salt thereof, is 100 mg to 480 mg daily.

Embodiment 18. The method of any one of Embodiments 1-12, wherein the therapeutically effective amount of ibudilast, or the pharmaceutically acceptable salt thereof, is selected from the group consisting of 30 mg/day, 40 mg/day, 50 mg/day, 60 mg/day, 90 mg/day, 100 mg/day, 110 mg/day, 120 mg/day, 150 mg/day, 180 mg/day, 190 mg/day, 200 mg/day, 210 mg/day, 240 mg/day, 270 mg/day, 300 mg/day, 360 mg/day, 400 mg/day, 440 mg/day, 480 mg/day, 520 mg/day, 580 mg/day, 600 mg/day, 620 mg/day, 640 mg/day, 680 mg/day, and 720 mg/day.

Embodiment 19. The method of any one of Embodiments 1-18, wherein the therapeutically effective amount is administered as a single dose or is divided into two, three, or four doses.

Embodiment 20. The method of any one of Embodiments 1-19, wherein ibudilast is administered continually.

Embodiment 21. The method of any one of Embodiments 1-20, wherein ibudilast, or the pharmaceutically acceptable salt thereof, is the only active agent administered to the patient.

Embodiment 22. The method of any one of Embodiments 1-20, wherein ibudilast, or the pharmaceutically acceptable salt thereof, is administered to the patient with at least one other active agent.

Embodiment 23. The method of Embodiment 22, wherein the at least one other active agent comprises a corticosteroid, a COX-2 (cyclooxygenase-2) inhibitor, a NSAID (non-steroidal anti-inflammatory drug), a SSRI (selective serotonin reuptake inhibitor), a SNRI (serotonin and norepinephrine reuptake inhibitor), a tricyclic antidepressant, an antihistamine, a beta-blocker, cannabidiol, ATP (adenosine triphosphate), ifenprodil tartrate, neurotropin, gabapentin, pregabalin, mirtazapine, or a combination of two or more thereof.

EQUIVALENTS

It should be understood that although the present disclosure has been specifically disclosed by certain embodiments and optional features, modification, improvement and variation of the disclosures embodied disclosed herein may be resorted to by those skilled in the art, and that such modifications, improvements and variations are considered to be within the scope of this disclosure. The materials, methods, and examples provided here are representative of certain embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

The use of the term "or" in the claims is used to mean "and/or" unless explicitly indicated to refer to alternatives only or the alternatives are mutually exclusive, although the disclosure supports a definition that refers to only alternatives and "and/or."

What is claimed is:

1. A method of treating post-COVID condition(s) in a SARS-COV-2 negative patient in need thereof, the method comprising administering to the patient a therapeutically effective amount of ibudilast to reduce TNFα or IL-6 cytokine, or a pharmaceutically acceptable salt thereof, wherein the post-COVID condition(s) comprise one or more of anxiety, fatigue, depression, shortness of breath, post-traumatic stress disorder, chest tightness, palpitations, smell or taste dysfunction, sleep difficulties, hair loss, or rash.

2. The method of claim 1, wherein the SARS-COV-2 negative patient further exhibits a post-COVID condition of cognitive impairment.

3. The method of claim 2, wherein the cognitive impairment includes one or both of memory lapse and impaired concentration.

4. The method of claim 1, wherein ibudilast, or the pharmaceutically acceptable salt thereof, is administered orally.

5. The method of claim 1, wherein ibudilast, or the pharmaceutically acceptable salt thereof, is administered intravenously.

6. The method of claim 1, wherein ibudilast, or the pharmaceutically acceptable salt thereof, is administered by subcutaneous injection or intramuscular injection.

7. The method of claim 1, wherein ibudilast, or the pharmaceutically acceptable salt thereof, is administered by inhalation.

8. The method of claim 1, wherein ibudilast, or the pharmaceutically acceptable salt thereof, is administered for 1, 2, 3, 4, 5, 6, 7, 8, 9, or 10 days, or more.

9. The method of claim 1, wherein ibudilast, or the pharmaceutically acceptable salt thereof, is administered for at least 2 months.

10. The method of claim 1, wherein ibudilast, or the pharmaceutically acceptable salt thereof, is administered at least once daily.

11. The method of claim 1, wherein ibudilast, or the pharmaceutically acceptable salt thereof, is administered twice daily.

12. The method of claim 1, wherein the therapeutically effective amount of ibudilast, or the pharmaceutically acceptable salt thereof, is from 0.1 mg to 720 mg per day.

13. The method of claim 1, wherein the therapeutically effective amount of ibudilast, or the pharmaceutically acceptable salt thereof, is at least 30 mg/day.

14. The method of claim 1, wherein the therapeutically effective amount of ibudilast, or the pharmaceutically acceptable salt thereof, is from 30 mg to 200 mg per day.

15. The method of claim 1, wherein the therapeutically effective amount of ibudilast, or the pharmaceutically acceptable salt thereof, is 60 mg to 600 mg daily.

16. The method of claim 1, wherein the therapeutically effective amount is administered as a single dose or is divided into two, three, or four doses.

17. The method of claim 1, wherein sleeping difficulties comprise insomnia.

18. The method of claim 1, wherein ibudilast, or the pharmaceutically acceptable salt thereof, is the only active agent administered to the patient.

19. The method of claim 1, wherein ibudilast, or the pharmaceutically acceptable salt thereof, is administered to the patient with at least one other active agent.

20. The method of claim 19, wherein the at least one other active agent comprises a corticosteroid, a COX-2 (cyclooxygenase-2) inhibitor, a NSAID (non-steroidal anti-inflammatory drug), a SSRI (selective serotonin reuptake inhibitor), a SNRI (serotonin and norepinephrine reuptake inhibitor), a tricyclic antidepressant, an antihistamine, a beta-blocker, cannabidiol, ATP (adenosine triphosphate), ifenprodil tartrate, neurotropin, gabapentin, pregabalin, mirtazapine, or a combination of two or more thereof.

\* \* \* \* \*